United States Patent [19]

Cuffe et al.

[11] 4,102,567

[45] Jul. 25, 1978

[54] MATERIAL FOR FABRICATION OF ARTIFICIAL INTRAOCULAR LENSES AND HARD CONTACT LENSES

[75] Inventors: Patricia M. Cuffe, Dudley; Albert R. LeBoeuf, Sturbridge; Edward A. Travnicek, Southbridge, all of Mass.

[73] Assignee: American Optical Corporation, Southbridge, Mass.

[21] Appl. No.: 722,961

[22] Filed: Sep. 13, 1976

[51] Int. Cl.² ............... B32B 27/30; B32B 27/36; G02C 7/04
[52] U.S. Cl. ................. 351/160; 351/162; 428/220; 428/336; 428/522; 526/329.7
[58] Field of Search ............ 351/160, 162; 3/13; 260/2.5 R, 2 R, 29.7 H; 428/220, 482, 483, 522, 523, 336; 526/329.7

[56] References Cited

U.S. PATENT DOCUMENTS

| | | | |
|---|---|---|---|
| 3,263,005 | 7/1966 | Emerick | 351/160 X |
| 3,586,423 | 6/1971 | Zeltzer | 351/162 X |
| 3,711,870 | 1/1973 | Deitrick | 3/13 |
| 3,776,230 | 12/1973 | Neefe | 351/162 X |
| 3,957,362 | 5/1976 | Mancini et al. | 351/160 |

FOREIGN PATENT DOCUMENTS

| | | | |
|---|---|---|---|
| 986,343 | 5/1976 | Canada | 351/162 |
| 1,916,629 | 10/1969 | Fed. Rep. of Germany | 351/162 |
| 1,004,424 | 9/1965 | United Kingdom | 351/162 |

OTHER PUBLICATIONS

Lowther, PMMA Material in Journal of the American Optometrists Association, Mar., 1976.

*Primary Examiner*—George F. Lesmes
*Assistant Examiner*—R. Eugene Varndell, Jr.
*Attorney, Agent, or Firm*—Jeremiah J. Duggan; Howard R. Berkenstock, Jr.

[57] ABSTRACT

Lens material suitable for ophthalmological use including implantation in the eye as an intraocular lens and as an ultra thin contact lens. The lenses are fabricated of polymethylmethacrylate (hereinafter PMMA) which PMMA is characterized by its very high molecular weight and almost complete freedom from strain. The PMMA may optionally be lightly cross-linked. The lens material is characterized by good machinability, color uniformity, and optical quality. It is substantially strain free and free from warpage when fabricated into extremely thin lenses.

4 Claims, 8 Drawing Figures

MATERIAL FOR FABRICATION OF ARTIFICIAL INTRAOCULAR LENSES AND HARD CONTACT LENSES

BACKGROUND OF THE INVENTION

1. Field of the Invention

This invention relates to improvements in ophthalmology and more particularly to artificial intraocular lenses (pseudophakoi) used for the correction of aphakia and re-establishment of binocularity in aphakia and to the fabrication of hard contact lenses arranged to be placed over the cornea. It further relates to improved methods of fabricating PMMA for subsequent fabrication of such lenses.

2. Discussion of the Prior Art

Well-fixed and well-centered intraocular lens implants are used to produce stable retinal images and re-establish binocularity in causes of aphakia. Many techniques of lens implantation exist including suturing to the ciliary muscle as disclosed in U.S. Pat. No. 3,711,870, iris diaphragm fixation as discussed in U.S. Pat. No. 3,673,616 and combinations of anterior and posterior iris clips as disclosed in U.S. Pat. Nos. 3,925,825 and 3,922,728. The lenses used in these various techniques are preferably fabricated of PMMA because of the easy machinability and proven physiological compatibility with the eye. Other materials which have been suggested include quartz and ophthalmic glass. Polymethylmethacrylate resins such as those available under the tradenames "LUCITE" and "PLEXIGLAS" and biologically neutral chemically pure polymeric materials in addition to the PMMA mentioned above but which are proven biologically inert, i.e., not susceptible to being absorbed by body fluids and capable of being well tolerated by the human body when implanted, have likewise been used. Comparable materials have been suggested for use in fabrication of hard contact lenses. "Hard" contact lenses are hereinafter distinguished from the so-called soft contact lenses which are characterized by hydration for usage. Generally, so-called soft contact lens compositions contain from 35 to 80 percent by weight of water when they are swelled to final dimension for usage. Hard contact lenses (and the hard polymerized precursor buttons from which soft contact lenses are made) are amenable to known machining, cutting and polishing techniques as described for example in U.S. Pat. Nos. 2,330,837, 3,227,507, 3,700,761 and others.

Machinability, color uniformity, and optical quality are properties to be desired in materials from which intraocular implant lenses and hard contact lenses are to be made. Especially in the case of hard contact lenses where it is desired to make lenses as thin as possible, it is desired that machinability be superior. Yet further, after machining, it is desired that the thin or ultra thin lenses be characterized by freedom from strain and warpage. Freedom from warpage is necessary to maintain the relative fit of the lens to the cornea and the net prescription which is ground or otherwise formed into the lens. In particular, it is desirable to make hard contact lenses as thin as possible to make them more comfortable to the wearer. To the best of our knowledge and belief, thin contact lenses to date have been on the order 0.12 millimeters thick on a commercial scale. Using concepts of the present invention, it is possible to make ultra thin hard contact lenses; that is, lenses on the order of 0.07 millimeters thick, depending in part, on the power of the lens.

After fabrication of the lenses, it is desirable they be free of strain. Strain is a phenomenon which can normally only be seen with polarized light. The strain appears as mottled colors or in maltese cross-like patterns. Such undesirable strain patterns can also be seen in some situations when being worn, for example, when worn in association with polarized sunglasses. In the case of both intraocular implants and hard contact lenses, it is desired that the rod from which buttons are cut (and the buttons themselves from which the lenses are machined) be capable of or exhibit substantially uniform coloration from one edge to the other. In this regard, it is desired that the rods from which the buttons are made be of substantially uniform dimension and roundedness.

Prior methods of preparing rods from which precursor contact lens and intraocular lens buttons were made have had a number of difficulties. One method which has proven itself highly successful for the fabrication of soft contact lenses is disclosed and claimed in our co-pending application entitled "Fabrication of Soft Contact Lens and Composition Therefor", Ser. No. 526,022 filed Nov. 21, 1974. That method included the usage of a polytetrafluoroethylene tube having positioned therein a sheet of polyethylene terephthalate film in spiral form. Polymer was cast within the film spiral. Monomer material leaked around the wrap and had other undesirable characteristics when attempts were made to cast PMMA in a comparable fashion. In attempting to overcome some of the difficulties encountered in trying to adopt the method of application Ser. No. 526,022, we tried glass tubes. The tubes were sealed from the atmosphere by appropriate plugs and nonoxidizing atmospheres. In one instance, we used a nitrogen filled balloon about the open end of the tube into which the monomer was cast. While the rods recovered from such a glass casting system were more uniform in composition, they were not more uniform in geometry, quite surprisingly. The rods recovered were noncircular in that they had flat areas along the length of the rod. Also, the glass tubes seemed to become more fragile with repeated use. While not able to fully understood the phenomenon by which this increase in fragility occurs, we postulate a fatigue was induced in the glass. This may have been due to leaching of minor constituents from the glass, or an accumulation of scratches during handling and cleaning.

In any event, we next tried metal tubes of stainless steel and aluminum. We selected these metal tubes becomes of the desirability of controlling the exothermic reaction which occurs when the PMMA is polymerizing. These metal tubes were also not entirely satisfactory. Among other things, noncircular flat areas formed on the cast rods and there was much sticking. Next, we tried tubes of Teflon. Teflon is the trademark of the DuPont Company for a waxy opaque material called polytetrafluoroethylene. This material has been used, for example, on cooking utensils and in many industrial applications to prevent sticking. The combination of teflon tubes within a copper or aluminum stiffener proved successful in accomplishing the objects of the invention; that is, the reproducible manufacture of a PMMA hard contact lens and intraocular lens precursor material characterized by good machinability, color uniformity and optical quality. Certain Teflon coatings on metal tubing has also accomplished this same end.

Accordingly, it is an object of the present invention to overcome the problems of intraocular implant and hard contact lens manufacture from PMMA precursor material. It is another object of the invention to provide an improved PMMA contact lens precursor of improved machinability, decreased strain, increased molecular weight, color uniformity, and optical quality and comfort during wear characterized by ultra thinness.

SUMMARY OF THE INVENTION

The aforesaid objectives and their corollaries are accomplished through the provision of a process for fabricating PMMA precursor rods and buttons. The rods are cast in an assembly including a combination of a Teflon tube and an exterior metal, preferably aluminum, stiffner. The assembly is characterized by a circular cylindrical space closed at one end arranged to receive the monomer to be polymerized. The polymerized monomer may be optionally lightly cross-linked or not cross-linked. Light cross-linking is preferably accomplished by using from about 0.2 to about 1.0 percent and preferably about 0.5 percent of a difunctional or polyfunctional cross-linking agent, for example, ethylene glycol dimethacrylate. The polymerization occurs in a temperature controlled water bath to ensure removal of heat generated during the exothermic reaction which occurs during polymerization. Contact lenses made from the rods cast in this manner are of excellent machinability, are uniform in color and are optically clear, but are capable of uniform coloration when desired. The coloration, if any, is produced by the inclusion of one or more suitable dyes or pigments in the monomer mixture. The lenses are of an ophthalmic quality and can be fabricated into ultra thin contact quality. The lenses are substantially strain free when viewed with polarized light. The foregoing method utilizes uniquely simple construction and is easily and economically practiced for the fabrication of either implantable intraocular lenses or hard contact lenses of PMMA. In one view, the lenses are free of striae and strain and are colorless (or uniform in color when dyed).

IN THE DRAWINGS

Details of the invention will become readily apparent to those skilled in the art from the following description when taken in conjunction with the accompanying drawings. In these drawings:

FIG. 1 is a photographic illustration of a strain pattern observed through use of polarized light when a lens or a lens blank is fabricated of PMMA according to this invention;

FIGS. 2a, b, c are photographic views of the strain pattern visible with use of polarized light in PMMA lenses fabricated according to prior art techniques;

DETAILED DESCRIPTION OF THE INVENTION AND PREFERRED EMBODIMENTS THEREOF

As mentioned above, one of the primary purposes of this invention is to supply means to make ultra thin hard contact lenses, i.e., lenses on the order of 0.07 millimeters in thickness. To do this, one must have extremely uniform material. In the case of rods from which precursor buttons are made, the rods must not only be chemically and physically homogeneous and uniform, they must be extremely uniform geometrically. The rods and buttons made therefrom must be strain free as determined from study with polarized light. The rods must be capable of uniform coloration in fabricating the rods; that is, during the polymerization of the monomer. No oxygen leakage (from the air or otherwise) should occur since oxygen retards free radical polymerization, which is an important aspect of this invention of fabricating PMMA characterized as very high molecular weight.

In the above description, we mention that aluminum is the preferred stiffener but other metals may be used with copper being a second preferred choice because of its good thermal conductivity and adequate corrosion resistance. We also mentioned the above that the tube geometry, or at least the space within which the rod is polymerized, must be of right circular cylindrical configuration. While the copper aluminum stiffener need not likewise be so precisely fabricated geometrically, it is to be desired in order to make temperature control during polymerization easier. The stiffener also prevents curvature formation during manufacture. We have also mentioned the use of 0.5 percent of a cross-linking agent in order to obtain our lightly cross-linked PMMA. This can range from 0.2 to about 1 percent.

It should be understood that a liner is not necessary. We can fabricate our improved PMMA in a self-supporting Teflon tube with plugs. A smooth interior surface is preferable. While the metal stiffeners are desirable since with them we can use longer Teflon tubes and thus make longer rods, shorter ones are perfectly acceptable without using the metal stiffeners. The metal alone cannot be used since it promotes sticking.

Figure 1:
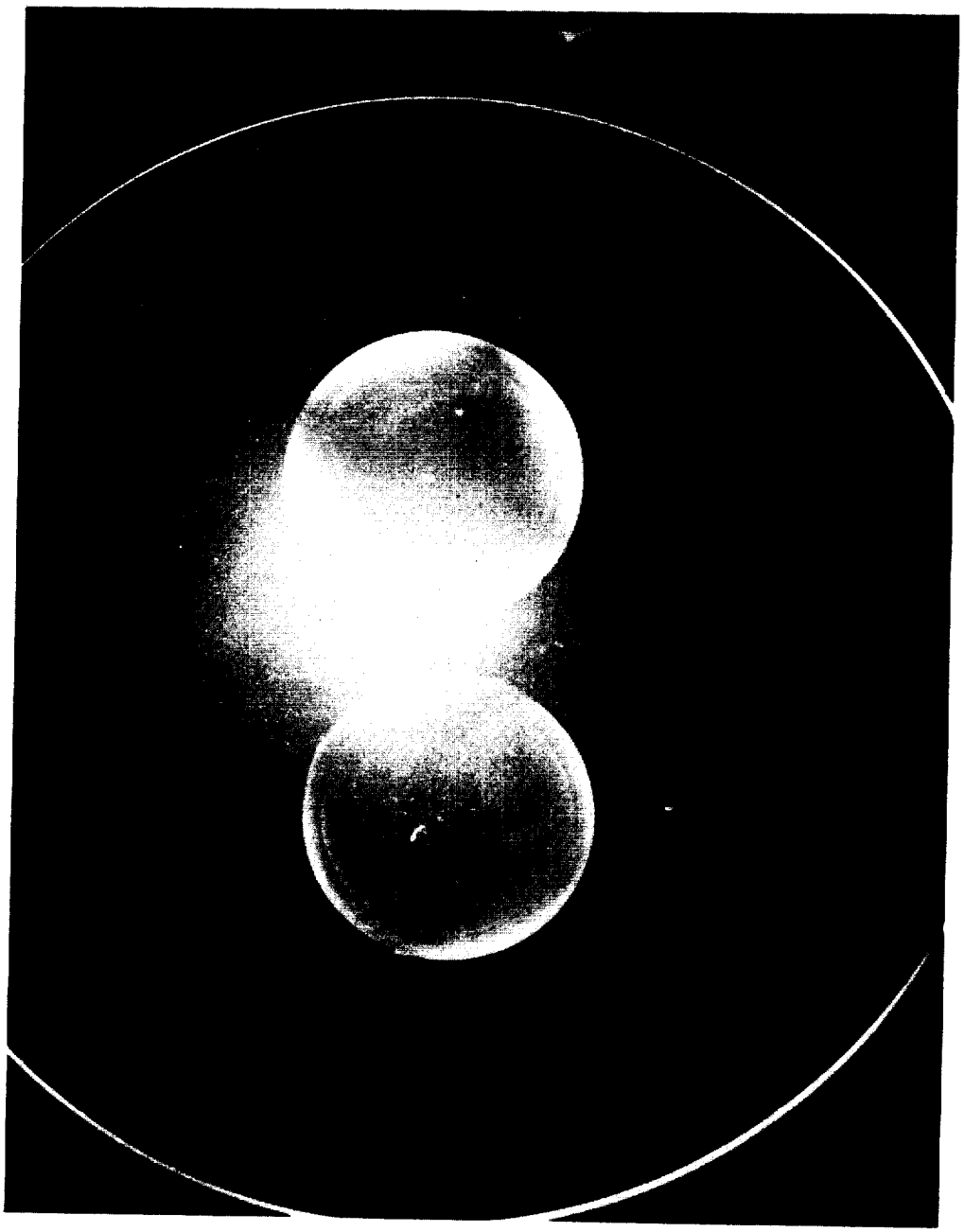
Figure 2A:
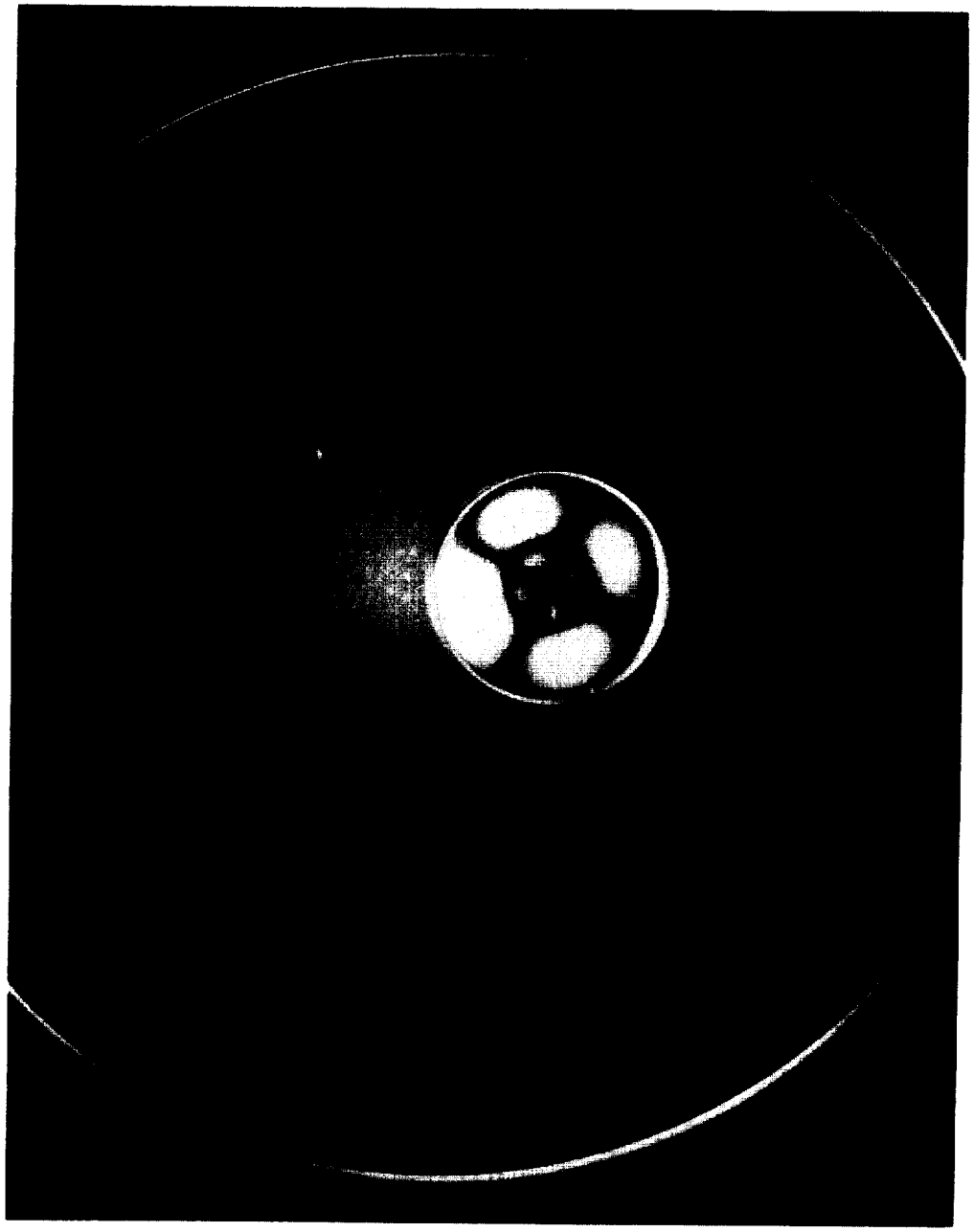
Figure 2B:
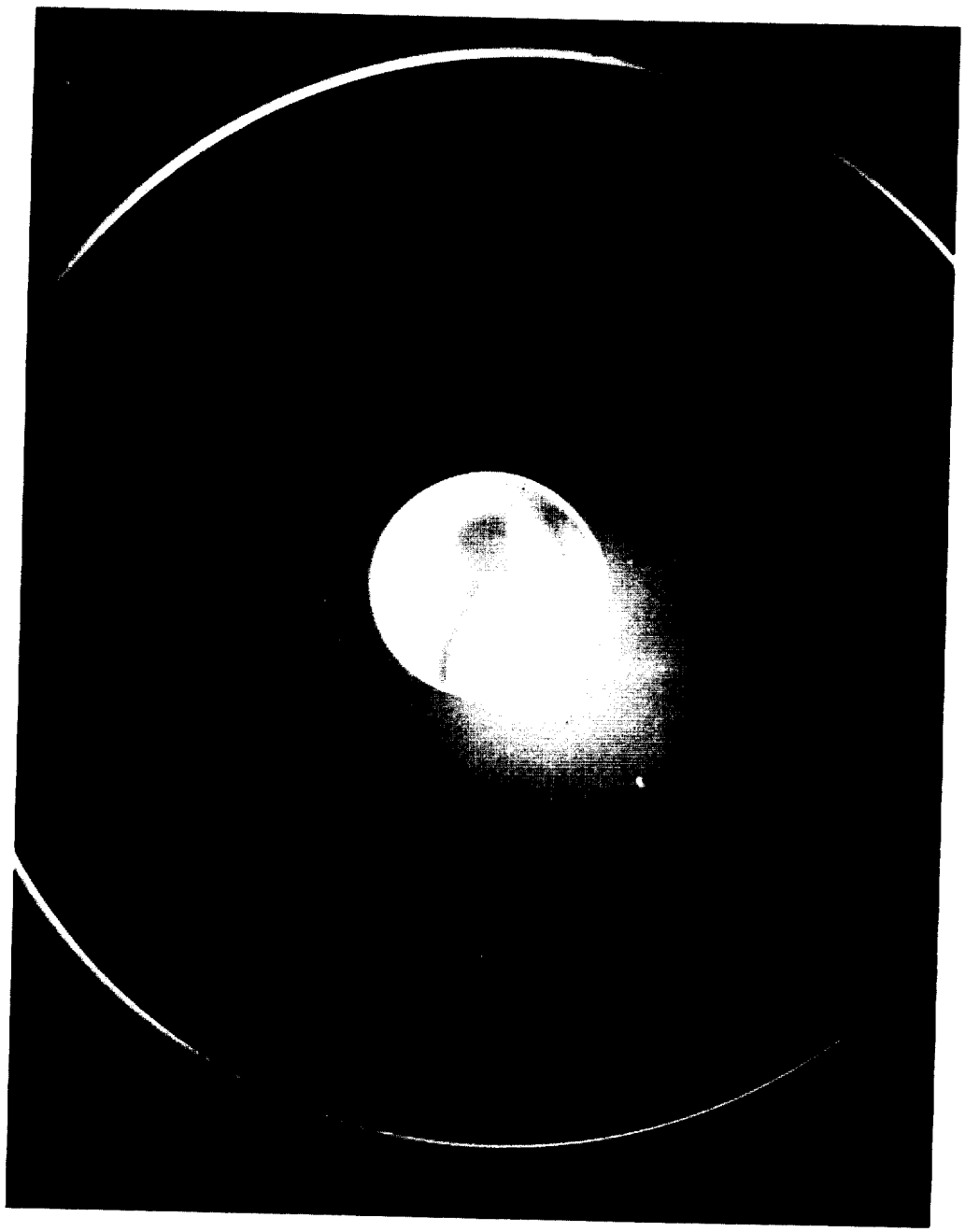
Figure 2C:

Referring to FIG. 1, there is shown a photograph of a strain pattern in a contact lens made from PMMA according to this invention as viewed through polarized light. Note the lack of patterns of the type seen in FIGS. 2a, b, and c. The buttons of FIGS. 2a, b, and c were fabricated similarly but in glass tubing. Distinct patterns are visible. The patterns in some respects look like a quartered circle with a smaller circumferential pattern of intermediate diameter. In many cases, the patterns are not symmetrical.

1. PRODUCT DESCRIPTION

Product fabricated according to the concepts of this invention is a polymerized polymethacrylate herein referred to as "PMMA" to maintain specification simplicity. Preferably, the PMMA is in the form of a cast rod. An intermediate product is a button machined from such a rod. A plurality of comparable buttons are machined from each rod. The rods may be of any convenient length. According to our experience, rods of either 2 or 4 feet lengths are easily handled and used in manufacture of hard contact lenses.

The physical dimensions of the buttons can be on the order of 0.5 inches in diameter which is a convenient diameter for contact lens manufacture. The buttons are preferably 0.14 inches in length. Acceptable tolerances are on the order of plus or minus 0.001 inches in each dimension. In practice, we find a yield of approximately 4 to 5 buttons per inch. The rods and resultant buttons can be made in the basic colors normally used in the contact lens business; namely, blue, gray, brown, green and colorless.

The monomer used in the preferred practice of this invention is methylmethacrylate and is purchased from the E. I. DuPont Company. It is sold under the trade designation "H-205 Methylmethacrylate." It is 99.8 percent methylmethacrylate monomer. An inhibitor may be present in an amount equivalent to 8 to 12 parts per million. The inhibitor is the mono-methyl ether of hydroquinone. There is less than 1 part per million of hydroquinone. The moisture content is a maximum of 0.03 percent. A maximum amount of 0.003 percent methacrylic acid may be present.

The preferred initiator used is di-sec butyl peroxydicarbonate (hereinafter SBP). The preferred cross-linking agent used is ethylene glycol dimethacrylate (hereinafter referred to as EDMA). The EDMA includes less than 100 parts per million of the methyl ether of hydroquinone, less than one part per million maximum of hydroquinone, and methacylic acid in an amount of less than 0.1 percent by weight. Dyes usable in the preferred practice of this invention will be discussed separately below.

Figures 3, 4:
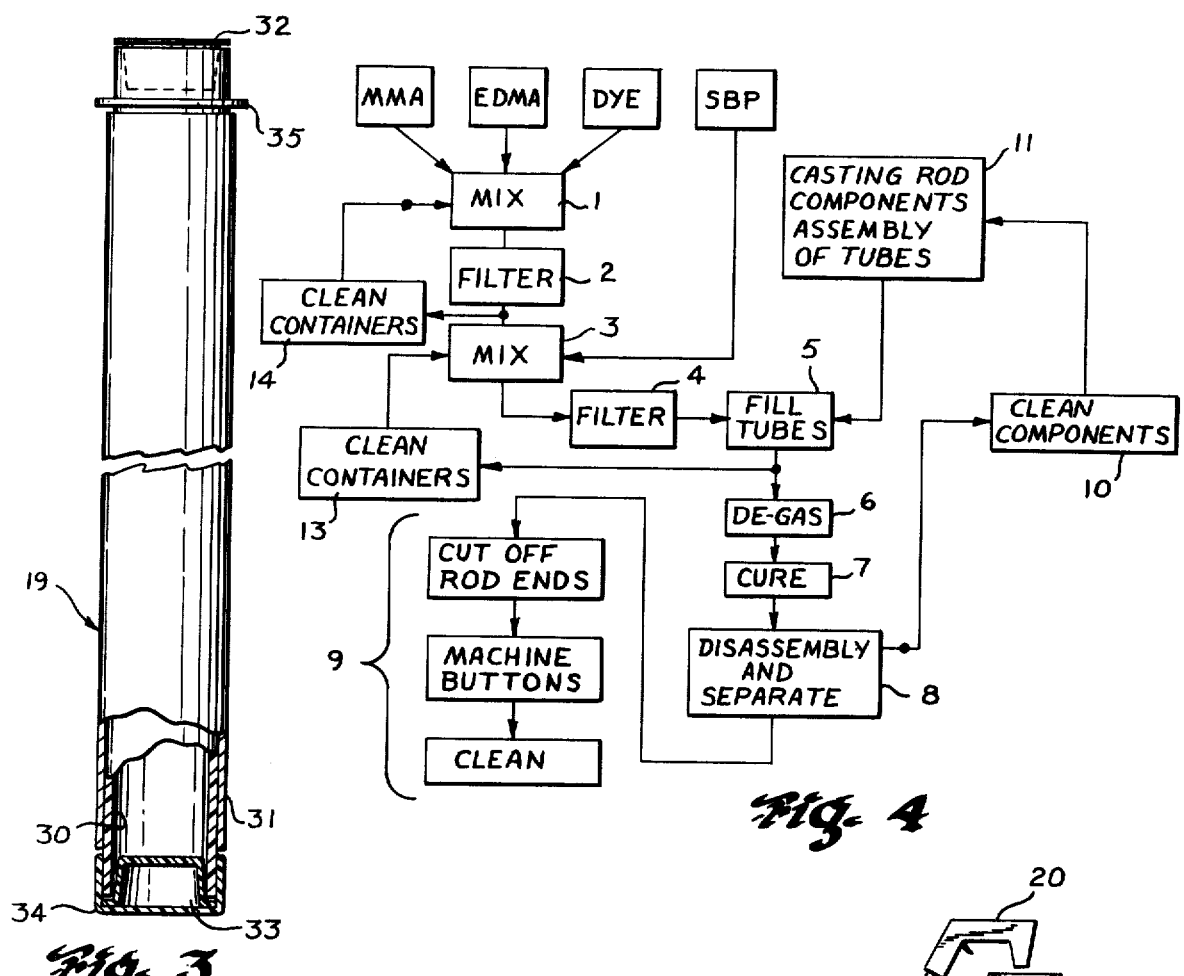
FIG. 3 is a perspective mean, with portions broken away, of casting tubes constructed according to this invention.
FIG. 4 is a schematic flow diagram of a process for fabricating PMMA intraocular lenses and hard contact lenses according to the present invention.

A batch of methylmethacrylate monomer according to the preferred embodiment of this invention, including the methylmethacrylate, EDMA, and SBP, is prepared as shown in the exemplary flow diagram FIG. 4. An exemplary batch analysis and the preferred mode now contemplated for mixing a 50 rod batch of PMMA (each rod being about 48 inches long) is as follows:

In preferred practice, the outlet from the filtration step is passed to a second pressure vessel at stage 3 to which the initiator is added and a second shorter mixing step of about 1 minute is conducted. Thereafter, the material is passed from the second mixing tank stage 2 to a second filtration stage 4 equivalent in all respects to the first one above described. As above, the material is conducted through polyethylene tubing. The polymer mix is now ready for casting into rods at station or stage 5 of FIG. 4. The rods should be cast as soon as possible after mixing and before polymerization has proceeded to any appreciable extent.

In preferred practice, the rods are cast in tubes which consist of double-walled units, the inner wall of which is a Teflon tube 30 (FIG. 3) approximately 4 feet long having an inside diameter of approximately 0.58 inches. Interior walls must be as smooth as conveniently possible to maintain the geometric control discussed above and to facilitate the removal of the cast rods. The outside diameter of the Teflon tubes is less critical and we used ones approximately ¾ inch in diameter. The metal tubing 31 which constitutes the second wall of the tubes is preferably aluminum (although the laboratory work herein discussed used copper tubes as well) approximately 4 feet in length, for example, we used 46 inch tubes which were about 2 inches shorter than the Teflon tubes used having an inside diameter of approximately 0.78 inch and being commercially characterized as type "L" hard copper tubing. In practice, it is slip fit over each Teflon tube. There are a pair of plugs 32 and 33 arranged to close the respective ends thereof. A collar 35 is fixed about one end of the Teflon tube 30 to facilitate support in a vertical position. The cap 34 is placed on plug 33. The plugs 32 and 33 are of conventional polyethylene. The outer cap is soft polyvinyl chloride. The plugs and cap are of a size capable of friction seat-

| Component | Parts by Weight | Typical Batch Weight, Grams | Weight Tolerance Percent | Weight Tolerance |
| --- | --- | --- | --- | --- |
| MMA Monomer | 100.00 | 10676.00 | ±1.0 | ±100 grams |
| EDMA | 0.50 | 53.38 | ±1.0 | ±0.5 gram |
| Blue Dye | 0.05 | 5.34 | ±0.50 | ±0.03 gram |
| SBP Initiator | 0.15 | 16.01 | ±1.0 | ±0.16 gram |

As is apparent, the exemplary batch is one used to prepare blue rods. Blue has been the most popular color for hard contact lens manufacture.

In practice, all containers and equipment are thoroughly cleaned, degreased, and dried prior to use. The batch ingredients, except the SBP initiator, are transferred to a first mixing container at stage 1 (FIG. 4) which is comprised of a 5 gallon container preferably of stainless steel (we used glass for the smaller batches made in the laboratory). The vessel is placed in position beneath an air-driven stirrer including a glass shaft and mixing rod. Mixing is carried out for a minimum of 45 minutes and the resulting mixed liquid is passed through polyethylene tubing to a 150 mm Whatman No. 4 filter in a 142 mm Milipore filter housing at stage 2. (The mixing vessel, during filtration, is placed at a line pressure of about 80 to 100 psi to force the liquid through the filters.) The air supply includes a suitable filter to assure that clean air is supplied to the pressure tank. The pressure tank, mixer, and filter are of conventional type and thus are not shown in the drawings in order to maintain simplicity of illustration and explanation.

ing on the ends of the tubes. The cap 34 is considered to "seal" the end on which it is placed from the water bath.

Figures 5, 5A:
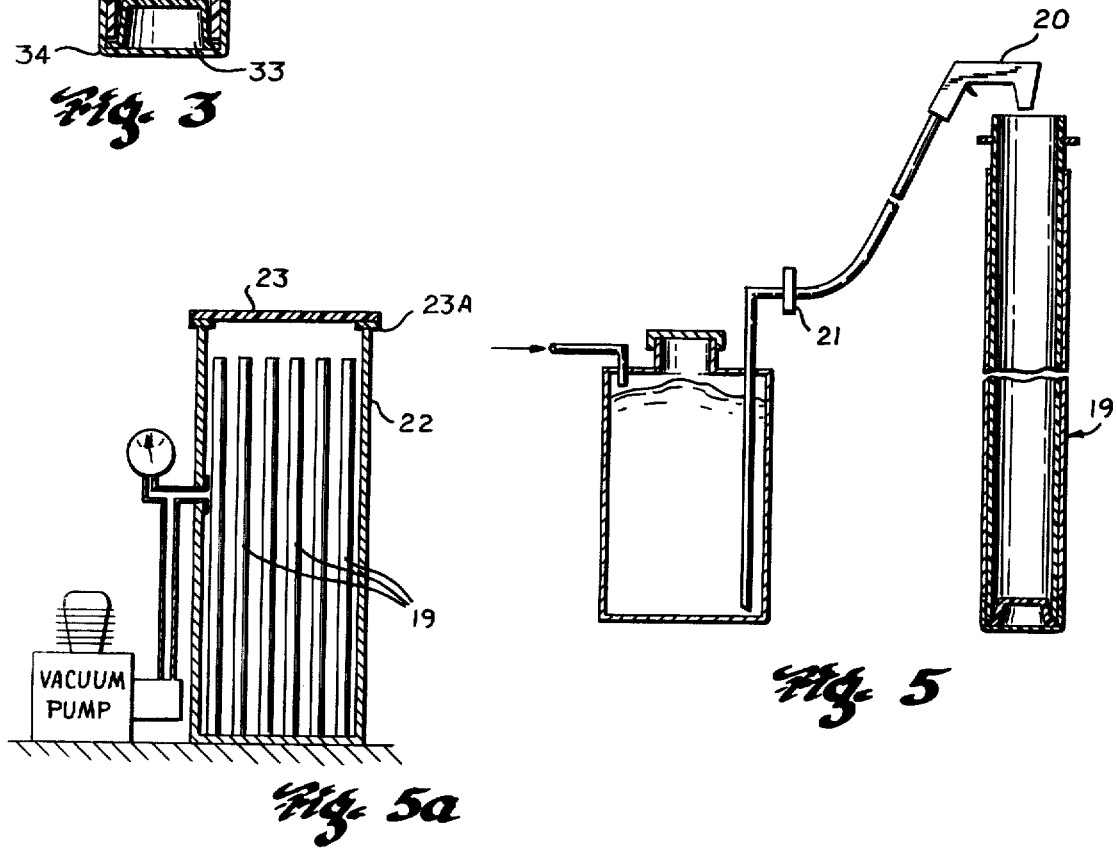
FIGS. 5 and 5a are schematic means of a filling and degassing station, respectively.

Monomer prepared in the manner described above is suitably poured into a group of the tubes at station 5 discussed. FIG. 5 is a schematic side elevation of a rod filling and degassing station utilizing the concepts of this invention. At the right, there is shown a tube 19 assembled in the manner just described supported in an upright or vertical manner adjacent to filling nozzle 20. The filling nozzle is interconnected through a Millipore filter 21 of the type above described by suitable polyethylene tubing with pressure vessel 3 above described. The pressure vessel contains mixed resin under 80–100 psi clean air pressure. A plurality of the tubes 19 are sealed in a vacumm chamber 22 by placing a second cap at the upper end or top after filling. In FIG. 5a, there is shown a plurality of such filled tubes 19 within a vacuum chamber covered by a suitable clear cap 23. In practice, the cap is approximately ¾ inch "Plexiglass" with a rubber gasket 23A to allow viewing of the degassing process which is the next step outlined in FIG. 4. A plurality of filled tubes are shown in the vacuum chamber. In FIG. 5A, a reduced pressure of about 30 to about 60 mm Hg absolute is drawn in the chamber. Actually, any pressure which will cause a steady or continual stream of gas bubbles to come to the surface of the liquid monomer in the tubes is sufficient. Great care must be taken to make this pressure reduction as slow as possible to prevent excessively fast bubbling which may cause overflow and spillage of monomer. In the preferred example being discussed herein, the pressure is held for approximately 10 minutes as a minimum. The vacuum is released and pressure allowed to rise to ambient conditions.

When the vacuum is relieved, the chamber cover is removed and the open end of each rod is lightly capped. Note the caps are not placed in such a manner as to seal the tops of the tubes. The tubes are removed from the degassing chamber and transferred to a filling rack ready for transfer to the water bath curing station. The water bath curing station consists of a suitable vessel, preferably stainless steel of sufficient volume to receive the 50 tubes in a rack supporting them. Water in the bath is maintained at a temperature of 27° C $\pm\frac{1}{2}$°C. According to the best mode now contemplated, the bath is sufficiently large to take 100 rods produced in the manner above described. This tank is 22½ inches in diameter, 48 inches high, filled with 45.5 inches of water. Without tubes, the tank is capable of holding a volume of 295.9 kilograms of water, and with tubes of the type above described the tank holds 251.1 kilograms of water.

In preferred practice, each of the tubes is filled with about 47 inches of MMA monomer which will make a rod about 41 inches long, untrimmed. This amounts to about 210 grams. The heat of polymerization of the MMA monomer is 13.8 K cal/g mole. That much monomer produces 2894 Kilo calories for complete polymerization. When one assumes zero heat capacity for the rods and tubes (not accurate) and if the water bath is perfectly insulated, i.e., adiabatic, (not true either) then the water temperature will increase 11.5° C during the polymerization cycle. Since we wish to maintain the water temperature at 27.0° C and assuming an air temperature of about 23.0° C, our water bath will lose heat at a rate of 94.7 K cal/hr. In our experience, the polymerization is complete in less than 20 hours for hard contact lenses, and 40 hours for PMMA for intraocular implant lenses. There are several choices or alternatives which one may use to control the temperature including increasing the size of the pool of water in which the rods are polymerized, or polymerizing fewer rods at one time, for example. We can tolerate some incremental increase in bath temperature. Alternatively, continuous supplemental cooling can be used, or there can be intermittent supplemental cooling with some manner of automatic temperature sensing device.

If supplemental cooling is used, which we suggest, very little will be needed, and care will be needed to prevent overcooling. If the bath has no inherent heat loss (which can be assumed for purposes of equipment design) and if the reaction proceeds at a maximum rate at one time of 10% conversion per hour, then the excess heat to be removed from the 100 rods will be 289. K cal/hr. which is equivalent to 337 watts or 1149 BTU/hr. If cooling water is used, which we suggest, and if it heats up from 15° C to 26° C, then the water flow rate should be 439 milliliters per minute or 0.1132 gallons per minute.

For a cooling coil, we suggest a piece of ¼ inch outside diameter copper tubing about 15 to 20 feet long. This provides about three turns around the inside wall of the tank. The cold water supply should include a small particle filter, a small throttling valve, a thermometer and a small rotameter to accurately show the flow rate so the flow can be controlled properly. All of these devices are conventional and are not shown in the drawings to maintain simplicity of illustration and explanation. Of course, too much cooling can overwhelm the heater and be wasteful of water and electricity.

An alternative method of controlling temperature is to have a thermostatic controller set about 0.3° C to 0.5° C above the heater set point and the controller operates a solenoid valve on the cold water supply to the cooling coil whenever the temperature reaches the upper set point temperature. This again is a conventional technique and is not explained, or illustrated, in detail to maintain drawing simplicity. A commercial constant temperature bath, which we suggest for the practice of this invention, is a Model No. 4-8605 manufactured by the American Instrument Company, Inc. of Silver Springs, Maryland.

The Teflon tubing, which we suggest is ⅜ inch outside diameter by ⅛ inch inside diameter reusable tubing and is available from a number off suppliers. The cap plugs, which we suggest, are ¼ inch sc and 6x sized manufactured by the Protective Closures Company of 215 Elmwood Avenue, Buffalo, New York. The glass mixing jars which we used were manufactured by the Glassed Products Company. The vacuum pump we used was a No. 1403B pump distributed by VWR Scientific Company. The pressure filter was likewise conventional and distributed by VWR Scientific Company.

Referring again to FIG. 4, which is a schematic process flow diagram for this invention, after curing in stage 7 (FIG. 4), the filled rods 19 are removed and disassembled and separated as schematically indicated at stage 8. The cast rods are then stored or cut into precursor buttons at stage 9. The hollow tubes are passed to stage 10 for cleaning and recycled through stage 11 to stage 5. As also shown in FIG. 4, the mixing containers are recycled through cleaning stage 13 and storage stage 14 to mixing stage 1. We have shown stage 9 schematically to include cutting off of the ends of the rods, which may be uneven due to contact with the caps on the ends, machining of the buttons from the rods, and cleaning.

Summarizing the polymerization procedure: a water bath is stabilized at 27° C $\pm\frac{1}{2}$° C and filled casting tubes are placed in the water bath. The water depth is checked to be certain the tubes are immersed with only the top 1 to 2 inches exposed above the water. Care must be taken to prevent the entry of water into the monomer mixture because it will cause inhomogeneities in the polymer rod. After the required time in the water bath, the polymerized rods are transferred to a forced circulating air oven for annealing. The air oven can be, for example, a Blue M stable therm oven, or equivalent. The annealing is with air at 45° $\pm$5°C for about 2 hours, then at 70° C $\pm$5° C for 1 hour and finally at 110° C $\pm$5° C for about 2 hours PMMA for hard contact lenses. For intraocular lens use, less residual monomer is desired so a longer annealing cycle is used. The cooling cycle is in air and includes initial cooling from the 100° elevated temperature at a rate of not over 20° C per hour. After the first 20° C drop, we may open the oven door and allow the rods to contact ambient room temperature conditions. The rods are removed from the oven, the cap plugs removed, the copper and Teflon tubes disassembled and cleaned (stage 8) and returned to storage (stage 11). The "annealing" may be termed post-curing.

The cast rods should then be inspected to see if any bubbles are visible. Bubbles may be removed by cutting out at the button-forming stage. Of course, too many bubbles in a given rod will cause rejection of the entire rod. Any rods which may excessively curve or warp after removal from the casting tubes are disposed of. If water has leaked into the casting tubes, a haze will show, and as before, hazy portions may be cut out and disposed of if limited.

As has been mentioned above, the present process is adapted to forming colored PMMA of the type especially suitable for contact lens manufacture. The preferred and most often used color is blue. A preferred batch for fabricating blue contact lenses, according to this invention, is as follows:

TABLE I

| DuPont (H205) MMA | 60.0 | grams |
|---|---|---|
| Sartomer EDMA | 0.3 | gram |
| Blue dye | .03 | gram |
| SBP | 0.09 | gram |

The preferred dye is a mixture of Acetosol blue GLST and Poly dye Blue GSFR.

For a gray colored contact lens, the following composition was used (all dyes manufactured by and purchased from Sandoz and Inmont):

TABLE II

| MMA | 180.0 | grams |
|---|---|---|
| EDMA | 0.90 | gram |
| Acetosol Blue GLST | .0450 | gram |
| Acetosol Red BLSN | .0414 | gram |
| Acetosol Yellow RLSN | .0027 | gram |
| Polydye Blue GSFR | .0009 | gram |
| SBP | .216 | gram |

For a green contact lens, we suggest the following batch composition:

TABLE III

| MMA | 180.0 | grams |
|---|---|---|
| EDMA | 0.9 | gram |
| Acetosol Blue GLST | .0642 | gram |
| Dermalight Red 2GL | .0504 | gram |
| Acetosol Yellow RLSN | .0276 | |
| SBP | .216 | |

For a brown contact lens, we suggest the following batch composition:

TABLE IV

| MMA | 180.0 | grams |
|---|---|---|
| EDMA | 0.9 | gram |
| Acetosol Blue GLST | .0933 | gram |
| Acetosol Red BLSN | .2031 | gram |
| Acetosol Yellow RLSN | .0636 | gram |
| SBP | 0.270 | gram |

In the foregoing discussion, we have disclosed and described in detail a preferred method for the fabrication of an improved PMMA rod stock for the fabrication of intraocular lenses and thin contact lenses. The improved PMMA allows one to manufacture thin contact lenses which do not exhibit undesirable warpage in use. The lenses are characterized by color uniformity, high molecular weight, and absence of strain patterns. The improved PMMA for contact lens use is characterized by light cross-linking. The rods are extremely uniform in physical and chemical properties. The rods of PMMA, cast according to the present invention, are characterized by right cylindrical geometrical cross-sectional configuration. This is a distinct departure from prior art methods of fabricating PMMA rod stock which included filling a plastic bag or tube and hanging more or less like smoked sausages for curing.

In the course of the work disclosed above, other possible plastics were considered and tested for the fabrication of the cylindrical forms in which the PMMA was cast. Polyolefins were tried and were found not as acceptable. The polyolefins are oxygen permeable and oxygen is an inhibitor of polymerization. However, polyolefins may be used as a coating for a metal stiffener, such as the aluminum or copper stiffener disclosed herein.

We have discussed aluminum and copper as the preferred stiffeners. Aluminum is preferable because of its light weight but eigher aluminum or copper is excellent because of high thermal conductivity and thus allowance for better water-bath control.

PMMA rod stock, fabricated according to this invention, is at least a 99% PMMA. Previous materials have analyzed at least 95% PMMA.

In the above description, we indicate there can be a difference in PMMA destined for contact lenses as distinguished from intra-ocular implant lenses. For example, we mention 20 hours cure time for hard contact lenses and 40 hours for implant lenses. We prefer to use a little less initiator in making the implant lens because we prefer a higher molecular weight in this non-cross-linked system. Actually, it is difficult to even discuss comparison to "molecular weight" with a non-cross-linked verses cross-linked system. In any event, we prefer the longer time period to get a heavier molecular system. The difference is probably insignificant.

Having thus described the invention in detail and with sufficient particularly to allow those skilled in the art to practice it, what is desired to have protected by letters patent is set forth in the following claims

We claim:

1. A thin hard optical lens of polymethylmethacrylate material of at least 99% polymethylmethacrylate characterized by good machinability, color uniformity, and optical quality, said material being characterized by having an average molecular weight of at least one million and substantial freedom from strain and free from warpage.

2. A substantially rigid polymethylmethacrylate lens according to claim 1 wherein said lens is lightly cross-linked.

3. The polymethylmethacrylate lens of claim 1 in the form of a contact lens of about 0.07 millimeter thickness.

4. A thin hard optical lens of claim 1, said lens being about 0.07 millimeter thickness and substantially free of strain patterns when viewed in polarized light.

* * * * *

UNITED STATES PATENT AND TRADEMARK OFFICE
CERTIFICATE OF CORRECTION

PATENT NO. : 4,102,567
DATED : July 25, 1978
INVENTOR(S) : Patricia M. Cuffe et al.

It is certified that error appears in the above-identified patent and that said Letters Patent are hereby corrected as shown below:

In column 2, lines 51 and 52, delete "becomes" and insert --because--;

In column 4, line 29, after "copper" and before "aluminum", insert --or--; and

In column 8, line 27, delete "sized" and insert --sizes--.

Signed and Sealed this

Twenty-ninth Day of May 1979

[SEAL]

Attest:

RUTH C. MASON
Attesting Officer

DONALD W. BANNER
Commissioner of Patents and Trademarks